United States Patent [19]

Kamiyama et al.

[11] 4,371,237
[45] Feb. 1, 1983

[54] APPARATUS FOR MEASURING CURVATURES OF A SPHERICAL SURFACE

[75] Inventors: Kiichi Kamiyama; Yoshinori Oana, both of Tokyo, Japan

[73] Assignee: Tokyo Kogaku Kikai Kabushiki Kaisha, Tokyo, Japan

[21] Appl. No.: 132,412

[22] Filed: Mar. 21, 1980

Related U.S. Application Data

[63] Continuation of Ser. No. 945,866, Sep. 26, 1978, abandoned.

[30] Foreign Application Priority Data

Sep. 30, 1977 [JP] Japan .................................. 52-117580
Sep. 30, 1977 [JP] Japan ............................. 52-131693[U]

[51] Int. Cl.³ ............................ A61B 3/10; A61B 3/00
[52] U.S. Cl. ..................................... 351/245; 351/205
[58] Field of Search ...................... 351/6, 7, 13, 16, 38; 356/124; 350/281

[56] References Cited

U.S. PATENT DOCUMENTS

| | | | |
|---|---|---|---|
| 1,776,960 | 9/1930 | Turville et al. | 351/12 |
| 3,253,509 | 5/1966 | Peters | 350/281 |
| 3,869,206 | 3/1975 | Nupuf | 351/13 |
| 3,932,030 | 1/1976 | Hasegawa et al. | 351/13 |

Primary Examiner—John K. Corbin
Assistant Examiner—Rodney Bovernick
Attorney, Agent, or Firm—Stevens, Davis, Miller & Mosher

[57] ABSTRACT

An actuating means for an ophthalmoscopic instrument wherein the adjustment knobs and handle are relatively located such that the knobs can be conveniently actuated by fingers of a hand gripping the handle.

3 Claims, 8 Drawing Figures

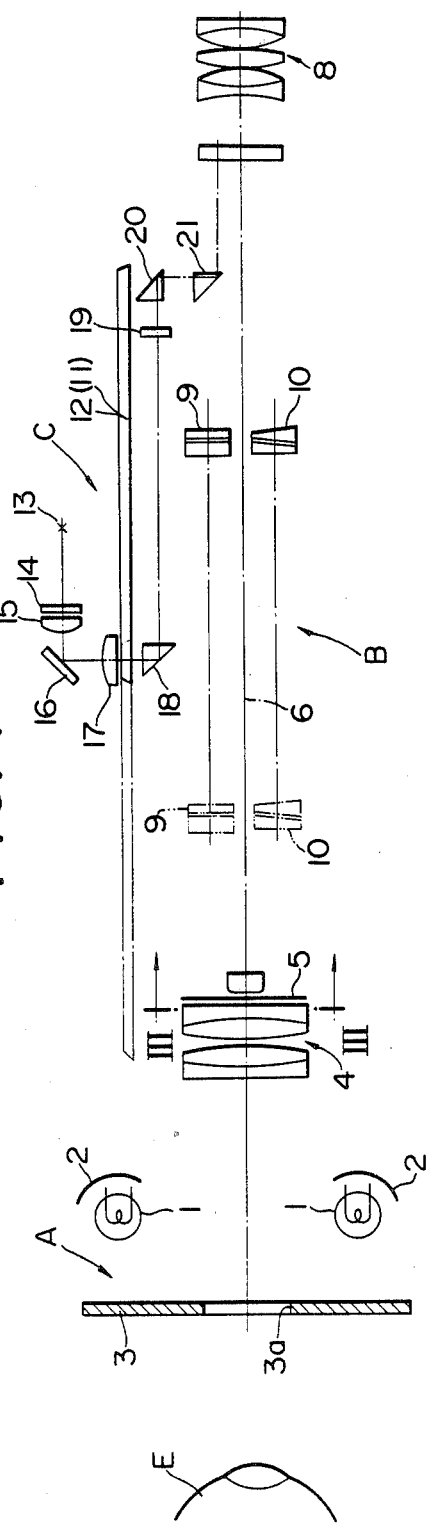
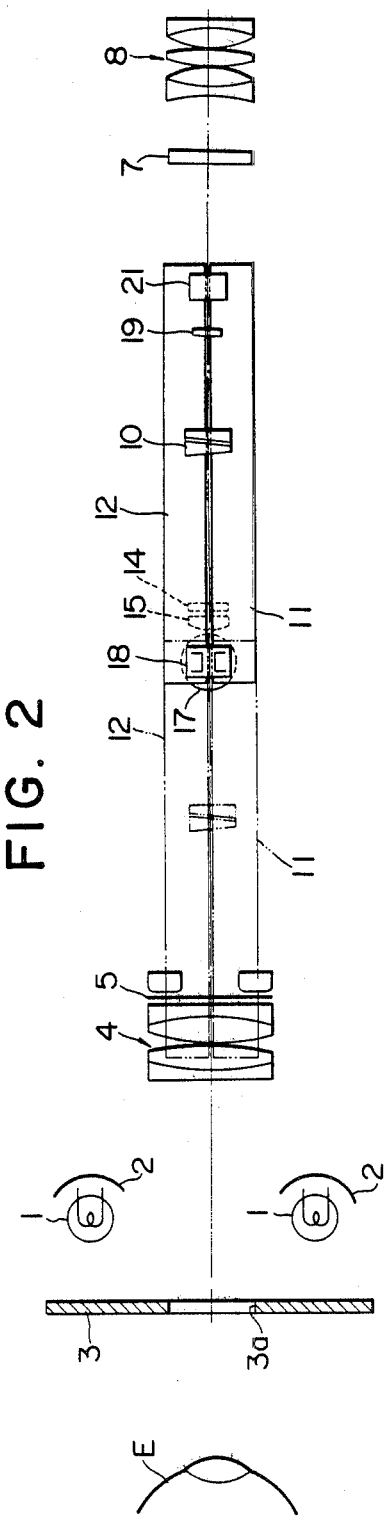

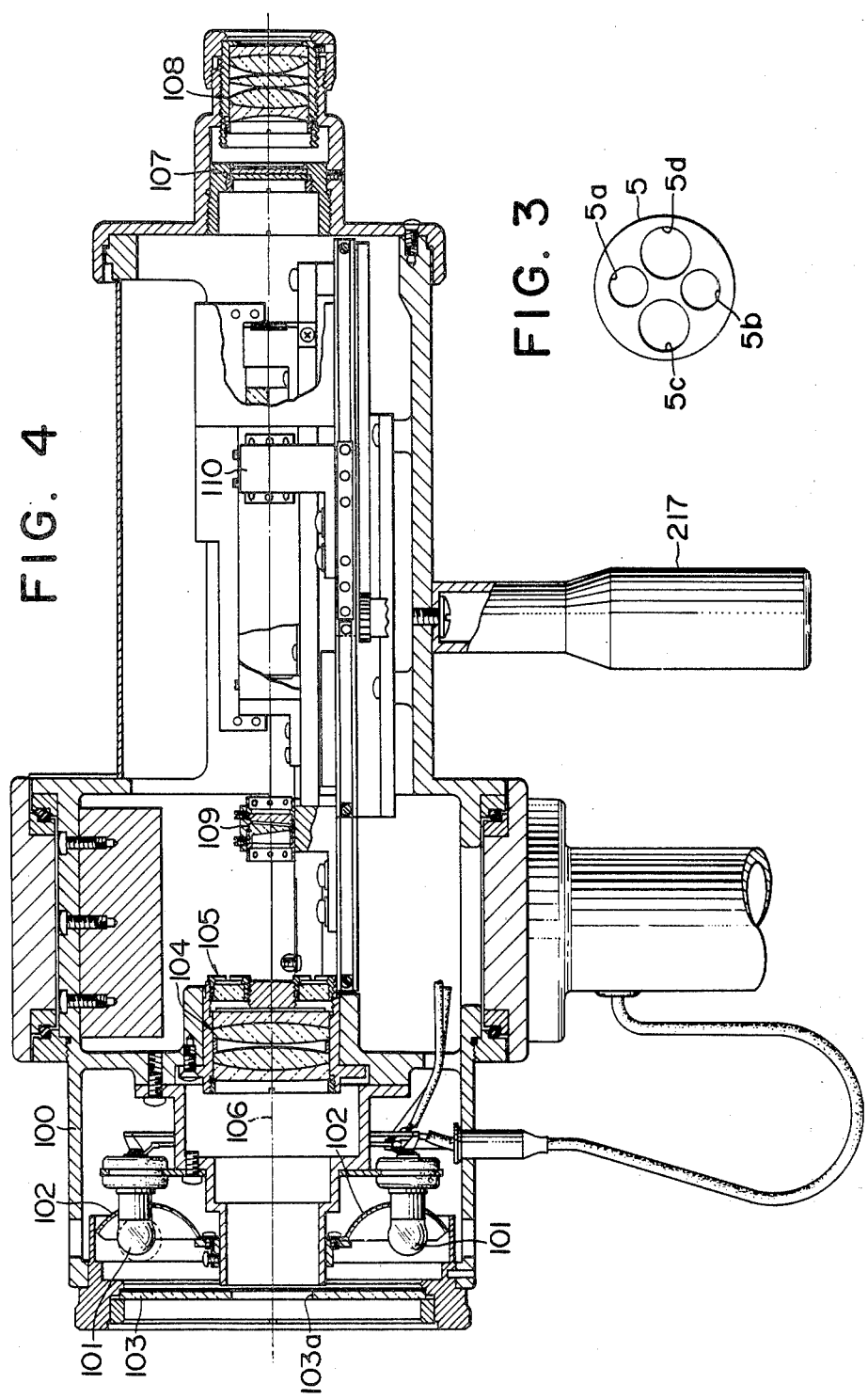

APPARATUS FOR MEASURING CURVATURES OF A SPHERICAL SURFACE

This is a continuation of application Ser. No. 945,866 filed Sept. 26, 1978 now abandoned.

The present invention relates to an apparatus for measuring curvature of spherical surface. More particularly, the present invention pertains to scale projecting means for such curvature measuring apparatus. The present invention is particularly applicable an apparatus for measuring the curvature of an eyeball of a patient or of a contact lens.

An apparatus for measuring the curvature of an eyeball is in general designed to observe through an observing optical system a target image projected on the surface of the cornea. The observing optical system generally comprises a vertical deflection prism and a horizontal deflection prism so that the light bundle which has been reflected at the cornea surface is deflected in both vertical and horizontal directions before it is focused on an image plane. The deflecting prisms are movable along the optical axis of the apparatus for placing the deflected target images at predetermined positions with respect to an undeflected target image which has not been passed through any of the deflecting prisms. The positions of the deflecting prisms are then indicated in terms of the curvature or radius of curvature.

In conventional apparatus, separate scale projecting optical systems have been provided for the vertical and horizontal deflecting prisms so that two different scales are projected on the same plane. In the conventional apparatus, however, it has been quite difficult to project the two scales with substantially the same brightness, substantially the same magnification and substantially the same focus. Further, it has also been difficult to eliminate any inclination between the two scales.

The present invention has therefore an object to eliminate the above problems and provide a structure which can readily be assembled and adjusted.

Another object of the present invention is to provide a curvature measuring apparatus which is easy to handle.

According to the present invention, the above and other objects can be accomplished by a curvature measuring apparatus comprising a target projecting system for projecting a target image on a spherical surface, an observing optical system including an image plane, a first lens system for focusing a light bundle as reflected at the spherical surface on the image plane and a second lens system for observing an image produced on the image plane, said observing optical system further including first deflecting means for deflecting the light bundle from the spherical surface in a first direction to produce a first deflected image and second deflecting means for deflecting the light bundle in a second direction which is perpendicular to the first direction to produce a second deflected image, said first and second deflecting means being movable along an optical axis of the observing optical system, adjusting means for moving the first and second deflected means along the optical axis so that said first and second deflected images are placed at predetermined positions with respect to an undeflected image, scale means including a first and second scales which are disposed adjacent to each other and adapted for designating the positions of the first and second deflecting means, respectively, scale projecting means for projecting said scale means, said scale projecting means including a single source of illumination for illuminating the first and second scales simultaneously and a scale projecting optical system for projecting light bundles from the scales.

Thus, the present invention is characterized by the fact that the scales for the first and second deflecting means are disposed adjacent to each other and illuminated by the same light source. In a preferable arrangement, the scales are projected on the image plane where the target images are projected. The scales may be provided on transparent plates so that they are projected by the lights which have passed through the transparent plates.

Preferably, said apparatus includes a body having a handle extending downwardly from a lower surface thereof, and said adjusting means includes a pair of adjusting knobs located one on each side of the handle, said adjusting knobs being provided at free ends thereof with means for removably attaching an extension knob, said extension knob being attached to one of said adjusting knobs. The arrangement provides convenient means for actuation by a single hand. For example, when it is desired to actuate by a right hand, the extension knob may be attached to the left side adjusting knob. On the other hand, for an actuation by a left hand, the extension knob may be attached to the right side adjusting knob.

The above and other objects and features of the present invention will become apparent from the following descriptions of a preferred embodiment taking reference to the accompanying drawings, in which;

FIG. 1 is a plan view of the optical system in the curvature measuring apparatus embodying the feature of the present invention;

FIG. 2 is a side view of the optical system shown in FIG. 1;

FIG. 3 is a view substantially along the line III—III in FIG. 1 for showing an aperture disc;

FIG. 4 is a sectional view of the curvature measuring apparatus in accordance with one embodiment of the present invention;

Figure 5:
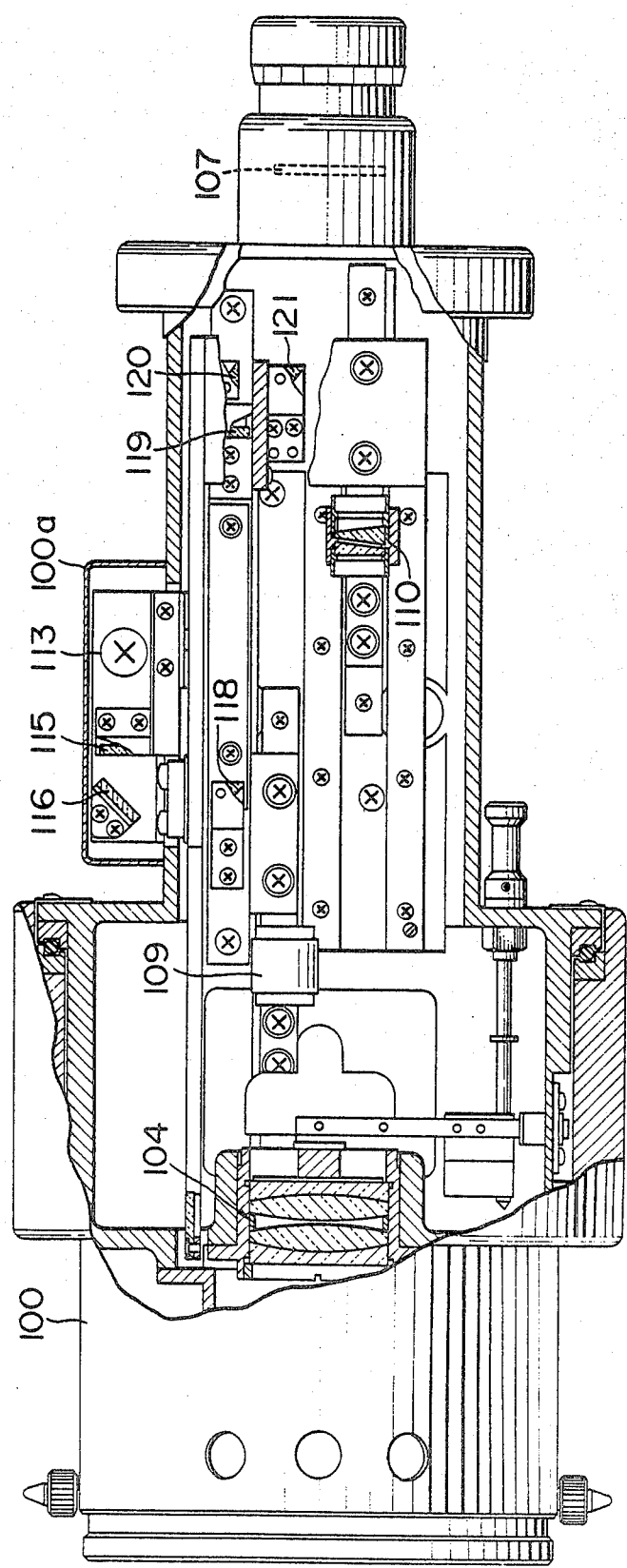
FIG. 5 is a partially cut-away plan view of the apparatus shown in FIG. 4.

Referring now to the drawings, particularly to FIGS. 1 and 2, the optical system shown therein includes a target projecting system A, an observing optical system B and a scale projecting system C. The target projecting system A comprises an illuminating light source 1, a condensing mirror 2 provided at the backside of the light source 1 and a target plate 3 located in front of the light source 1. The target plate 3 has a transparent target pattern so that the light from the source 1 is passed through the target pattern to produce a target image on a patient's eye E. When it is desired to measure the curvature of a contact lens, it may be located in the place of the eye E. The target plate 3 has an aperture 3a at the center thereof so that the light bundle of the target image as reflected at the cornea surface is passed through the aperture 3a into the observing optical system B.

The observing optical system B includes an objective lens 4 and an aperture plate 5 located behind the objective lens 4. The aperture plate 5 has four apertures 5a, 5b, 5c and 5d as shown in FIG. 3 so that the light from the lens 4 is passed through the apertures along the optical axis 6 and focused on an image plate 7. The image on the plate 7 is observed by an eye lens 8.

Between the aperture plate 5 and the image plate 7, there are disposed a vertical deflecting prism 9 and a horizontal deflecting prism 10 which respectively correspond to the apertures 5c and 5d of the plate 5. The prisms 9 and 10 functions to deflect the light bundles which have passed through the apertures 5c and 5d respectively in vertical and horizontal directions. The prisms 9 and 10 are movable along the optical axis 6 so that any movements of the prisms 9 and 10 cause changes in positions on the image plate 7 of the light bundles which have passed through the apertures 5c and 5d. As well known in the art, the curvatures of the cornea surface of the eye E are measured in terms of the positions of the prisms 9 and 10 with respect to the images of the light bundles which have passed through the apertures 5a and 5b.

The scale projecting system includes a vertical scale plate 11 connected with the vertical deflecting prism 9 and a horizontal scale plate 12 connected with the horizontal deflecting prism 10. The scale plates 11 and 12 are positioned adjacent and parallel with each other and movable in the longitudinal directions together with the prisms 9 and 10, respectively. In order to project the scales on the scale plates 11 and 12, there is provided a light source 13 in such a manner that the light from the light source 13 is directed through a filter 14, a first condenser lens 15, a reflecting mirror 16 and a second condenser lens 17 to the scale plates 11 and 12. The light which has passed through the scale plates 11 and 12 are then reflected by a prism 18 to a projecting lens 19 which projects the light through prisms 20 and 21 to the image plate 7. The projected images of the scales are then observed through the eye lens 8. It should be noted that, in the above scale projecting system C, the two scales are illuminated by the same light source so that there will be no problem of adjusting the brightness and the focus of the scale images and of correcting the inclinations of the scale images.

Figure 6:
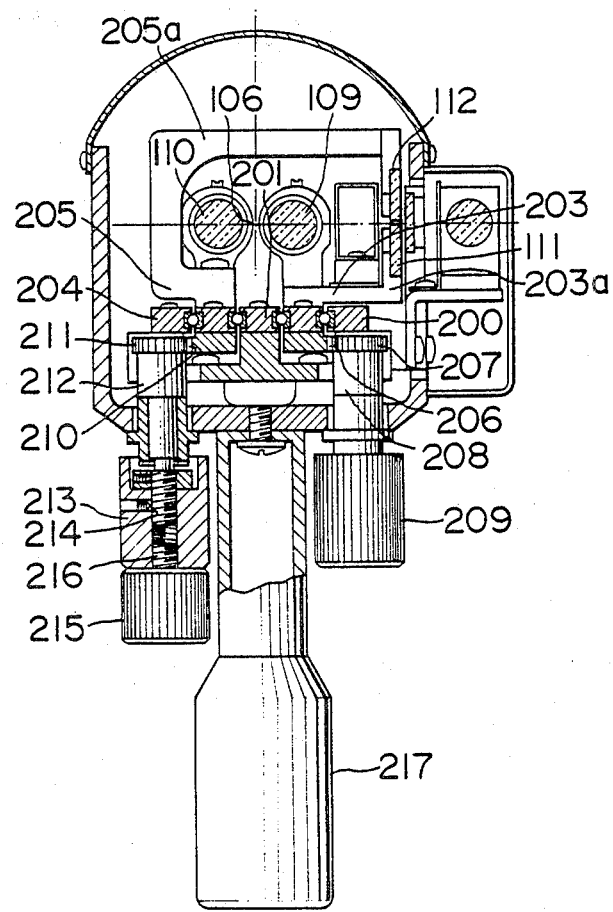
FIG. 6 is a vertical sectional view of the apparatus.

FIGS. 4 through 6 show a specific embodiment having the aforedescribed optical system. The eye curvature measuring apparatus shown therein includes a case 100 having a front end portion which houses an illuminating light source 101, a condensing reflector 102 and a target plate 103 provided with a central aperture 103a. Behind the target projecting system, there is provided an objective lens 104 having an optical axis 106 and, along the optical axis 106, there is an aperture plate 105 which is secured to the tube of the objective lens 104. At the rear portion of the case 100, there are disposed an image plate 107 and an eye lens 108.

At one side of the optical axis 106, there is a vertical deflecting prism 109 and at the other side a horizontal deflecting prism 110. The prism 109 is carried on a support member 203 which is movable between paired guide rails 200 and 201 in a direction parallel with the optical axis. The support member 203 has a transversely extending arm 203a which carries a vertical deflection scale plate 111. Similarly, the prism 110 is carried by a support member 205 which is movable between paired guide rails 201 and 204 in a direction parallel with the optical axis 106. The member 205 has an arm 205a which extends transversely above the optical axis 106 and a horizontal scale plate 112 is attached to the arm 205a.

As shown in FIG. 5, the case 100 is provided at a side with a cover 100a and inside of the cover 100a there are provided a scale projecting light source 113, a condenser lens 115 and a reflector 116 so that the light from the source 113 is reflected by the reflector 116 and then passed through the scale plates 111 and 112 to a prism 118 in the case 100. The light is then reflected by the prism 118 and passed through a projecting lens 119, prisms 120 and 121 to the image plate 107.

Referring to FIG. 6, the support member 203 for the deflecting prism 109 is formed at its side surface with a rack 206 which is engaged with a pinion 207 having a shaft 208 extending downwardly beyond the lower surface of the case 100. An adjusting knob 209 is secured to the lower end of the shaft 208. It will therefore be noted that a rotation of the knob 209 causes a movement of the prism 109 in the direction parallel with the optical axis 106.

Similarly, the support member 205 for the deflecting prism 110 is formed with a rack 210 which is engaged with a pinion 211 having a shaft 212 extending downwardly beyond the lower surface of the case 100. An adjusting knob 213 similar to the knob 209 is secured to the lower end of the shaft 212. The adjusting knobs 209 and 213 are respectively formed with axially extending threaded bores 214 and, in the case shown in FIG. 6, an extension knob 215 is threaded at its screw shaft 216 into the threaded bore 214 of the knob 213. Between the adjusting knobs 209 and 213, there is a handle 217 which is secured to the case 100.

Figure 7:
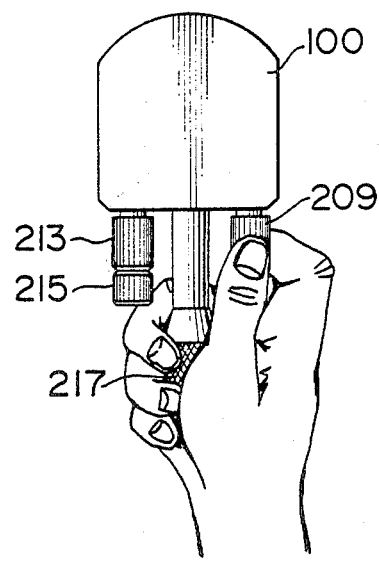
FIGS. 7 and 8 are perspective views showing the manner of actuating the adjusting knobs.
Figure 8:
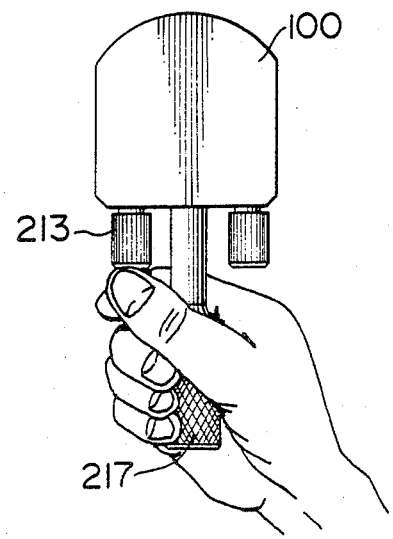

FIGS. 7 and 8 show a single hand operation by using a right hand. The operator grips the handle 217 and actuates the knob 209 by the thumb and the forefinger as shown in FIG. 7. When it is desired to the knob 213 with the handle gripped by the same hand, the operator may actuate the extension knob 215 as shown in FIG. 8. It is thus unnecessary to change the grip for actuating both of the knobs 209 and 213.

When it is intended to perform a single hand actuation by using a left hand, the extension knob 215 is removed from the adjusting knob 213 and attached instead to the adjusting knob 209.

The invention has thus been shown and described with reference to a specific embodiment, however, it should be noted that the invention is in no way limited to the details of the illustrated structures but changes and modifications may be made without departing from the scope of the appended claims.

We claim:

1. A single hand actuating means for an ophthalmoscopic instrument having a body and means mounting said body for swingable adjustment and at least two adjusting devices provided in the body, said adjusting devices being connected to first and second movable optical elements, said body being provided with a downwardly extending handle for the swingable adjustment of the body, a pair of adjusting knobs provided on said body at the opposite sides of the handle and connected with respective ones of the adjusting devices, one of said adjusting knobs being longer than the other knob whereby the knobs can conveniently be actuated by fingers of a hand gripping the handle.

2. A single hand actuating means in accordance with claim 1, in which said adjusting knobs have base portions of the same lengths, an extension knob which is removably attached to one of the base portions to provide the knob of larger length, the other of the base portion being also provided with means for removably attaching the extension knob.

3. An ophthalmoscopic instrument including a first deflecting means for deflecting a light bundle from a surface to produce a first deflected image, and a second deflecting means for producing a second image, said first and second deflecting means being movable along an optical axis of an observing optical system, said instrument having a housing and means mounting said housing for swingable adjustment, said housing supporting a vertically extending handle, said housing having first and second adjusting knobs located on each side of said handle, within reach of said handle by the fingers of a hand holding said handle, said adjusting knobs being connected to said first and second deflecting means whereby said deflecting means are adjustable with the fingers of a single hand holding said handle.

* * * * *